US008383423B2

(12) United States Patent
Weiss et al.

(10) Patent No.: US 8,383,423 B2
(45) Date of Patent: *Feb. 26, 2013

(54) PEPTIDE-COATED NANOPARTICLES WITH GRADED SHELL COMPOSITIONS

(75) Inventors: Shimon Weiss, Los Angeles, CA (US); James M. Tsay, Los Angeles, CA (US); Fabien Pinaud, Los Angeles, CA (US); Soren Doose, Bielefeld (DE)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/074,209

(22) Filed: Mar. 29, 2011

(65) Prior Publication Data
US 2011/0195126 A1 Aug. 11, 2011

Related U.S. Application Data

(63) Continuation of application No. 11/630,584, filed as application No. PCT/US2005/022102 on Jun. 20, 2005, now Pat. No. 7,943,396.

(60) Provisional application No. 60/581,828, filed on Jun. 22, 2004.

(51) Int. Cl.
*G01N 33/551* (2006.01)

(52) U.S. Cl. ......................... 436/524; 436/525

(58) Field of Classification Search .................. None
See application file for complete search history.

(56) References Cited

U.S. PATENT DOCUMENTS

| | | | |
|---|---|---|---|
| 4,795,698 A | 1/1989 | Owen et al. | |
| 5,186,827 A | 2/1993 | Liberti et al. | |
| 5,200,084 A | 4/1993 | Liberti et al. | |
| 5,262,357 A | 11/1993 | Alivisatos et al. | |
| 5,466,574 A | 11/1995 | Liberti et al. | |
| 5,505,928 A | 4/1996 | Alivisatos et al. | |
| 5,512,332 A | 4/1996 | Liberti et al. | |
| 5,541,072 A | 7/1996 | Wang et al. | |
| 5,567,326 A | 10/1996 | Ekenberg et al. | |
| 5,698,271 A | 12/1997 | Liberti et al. | |
| 5,751,018 A | 5/1998 | Alivisatos et al. | |
| 5,795,470 A | 8/1998 | Wang et al. | |
| 5,866,099 A | 2/1999 | Owen et al. | |
| 5,990,479 A | 11/1999 | Weiss et al. | |
| 6,114,038 A | 9/2000 | Castro et al. | |
| 6,120,856 A | 9/2000 | Liberti et al. | |
| 6,194,213 B1 | 2/2001 | Barbera-Guillem | |
| 6,207,392 B1 | 3/2001 | Weiss et al. | |
| 6,221,602 B1 | 4/2001 | Barbera-Guillem et al. | |
| 6,261,779 B1 | 7/2001 | Barbera-Guillem et al. | |
| 6,274,323 B1 | 8/2001 | Bruchez et al. | |
| 6,306,610 B1 | 10/2001 | Bawendi et al. | |
| 6,319,607 B1 | 11/2001 | Barbera-Guillem et al. | |
| 6,326,144 B1 | 12/2001 | Bawendi et al. | |
| 6,333,110 B1 | 12/2001 | Barbera-Guillem | |
| 6,365,362 B1 | 4/2002 | Terstappen et al. | |
| 6,423,551 B1 | 7/2002 | Weiss et al. | |
| 6,444,143 B2 | 9/2002 | Bawendi et al. | |
| 6,468,808 B1 | 10/2002 | Nie et al. | |
| 6,544,732 B1 | 4/2003 | Chee et al. | |
| 6,620,627 B1 | 9/2003 | Liberti et al. | |
| 6,623,982 B1 | 9/2003 | Liberti et al. | |
| 6,630,307 B2 | 10/2003 | Bruchez et al. | |
| 6,645,731 B2 | 11/2003 | Terstappen et al. | |
| 6,649,138 B2 | 11/2003 | Adams et al. | |
| 6,767,702 B2 | 7/2004 | Mirkin et al. | |
| 6,777,186 B2 | 8/2004 | Mirkin et al. | |
| 6,794,265 B2 * | 9/2004 | Lee et al. ................ | 438/409 |
| 6,815,064 B2 | 11/2004 | Treadway et al. | |
| 6,838,243 B2 | 1/2005 | Lai et al. | |
| 6,955,855 B2 | 10/2005 | Naasani | |
| 7,172,791 B2 | 2/2007 | Treadway et al. | |
| 7,198,847 B2 | 4/2007 | Naasani | |
| 7,205,048 B2 | 4/2007 | Naasani | |
| 7,214,428 B2 | 5/2007 | Naasani | |
| 7,368,086 B2 | 5/2008 | Naasani | |
| 7,943,396 B2 * | 5/2011 | Weiss et al. ............. | 436/524 |
| 2001/0034034 A1 | 10/2001 | Bruchez et al. | |
| 2002/0009728 A1 | 1/2002 | Bittner et al. | |
| 2002/0028457 A1 | 3/2002 | Empedocles et al. | |
| 2002/0127224 A1 | 9/2002 | Chen | |
| 2002/0150905 A1 | 10/2002 | Barbera-Guillem et al. | |
| 2003/0008414 A1 | 1/2003 | Nie et al. | |
| 2003/0027214 A1 | 2/2003 | Kamb | |
| 2003/0082237 A1 | 5/2003 | Cha et al. | |
| 2003/0099940 A1 | 5/2003 | Empedocles et al. | |
| 2003/0113709 A1 | 6/2003 | Alivisatos et al. | |
| 2003/0129590 A1 | 7/2003 | Rosenthall et al. | |
| 2003/0129591 A1 | 7/2003 | Rosenthall et al. | |

(Continued)

FOREIGN PATENT DOCUMENTS

| | | |
|---|---|---|
| GB | 2342651 | 4/2000 |
| JP | 2002-525394 | 8/2002 |
| WO | WO-00/17655 | 3/2000 |
| WO | WO-00/27365 | 5/2000 |
| WO | WO-2004/039830 A2 | 5/2004 |
| WO | WO-2004/039830 A3 | 2/2005 |
| WO | WO-2005/053649 A1 | 6/2005 |
| WO | WO-2005/093422 A2 | 10/2005 |
| WO | WO-2005/093422 A3 | 2/2006 |
| WO | WO-2006/093516 A2 | 9/2006 |

OTHER PUBLICATIONS

International Search Report dated Nov. 7, 2006, issued in PCT/US2005/22102.
PCT/US2005/009344 "Notification Concerning Transmittal of Int'l Prelim. Report on Patentability" and "Written Opinion of the ISA," mailed Oct. 5, 2006.

(Continued)

*Primary Examiner* — Chris L Chin
(74) *Attorney, Agent, or Firm* — Venable LLP; Michael A. Gollin; Lars H. Genieser

(57) ABSTRACT

A peptide-coated nanoparticle that includes a nanocrystal surrounded by a graded shell that is composed of at least two different semiconductor molecules. At least one peptide is attached to the surface of the graded shell to render the nanoparticle biocompatible. The nanocrystal core and graded shell are optionally annealed with ultra violet radiation prior to and/or after attachment of the peptide(s).

18 Claims, No Drawings

U.S. PATENT DOCUMENTS

| | | | |
|---|---|---|---|
| 2003/0148544 | A1 | 8/2003 | Nie et al. |
| 2003/0165951 | A1 | 9/2003 | Bruchez, Jr. et al. |
| 2003/0175773 | A1 | 9/2003 | Chee et al. |
| 2004/0007169 | A1 | 1/2004 | Ohtsu et al. |
| 2004/0009911 | A1 | 1/2004 | Harris et al. |
| 2004/0014060 | A1 | 1/2004 | Hoheisel et al. |
| 2004/0023415 | A1 | 2/2004 | Sokolov et al. |
| 2004/0038307 | A1 | 2/2004 | Lee et al. |
| 2004/0158051 | A1 | 8/2004 | Ozkan et al. |
| 2004/0166505 | A1 | 8/2004 | Bruchez et al. |
| 2004/0171039 | A1 | 9/2004 | Bruchez et al. |
| 2004/0180380 | A1 | 9/2004 | Lee et al. |
| 2005/0054004 | A1 | 3/2005 | Alivisatos et al. |
| 2005/0059031 | A1 | 3/2005 | Bruchez et al. |
| 2007/0172427 | A1 | 7/2007 | Barchi et al. |
| 2008/0039816 | A1 | 2/2008 | Svarovsky et al. |
| 2009/0253211 | A1 | 10/2009 | Weiss et al. |

OTHER PUBLICATIONS

International Search Report, date, issued in PCT/US2003/34897, mailed Aug. 20, 2004.

International Search Report and Written Opinion of the International Searching Authority, issued in PCT/US2005/009344, mailed Dec. 21, 2005.

International Preliminary Report on Patentability, issued in PCT/US2005/009344, mailed Oct. 5, 2006.

International Preliminary Examination Report in PCT/US2003/014401, dated Feb. 5, 2005.

International Preliminary Report on Patentability in PCT/US2005/022102, dated Dec. 28, 2006.

Written Opinion of International Search Authority in PCT/US2005/022102, dated Nov. 7, 2006.

Michalet et al. Properties of Fluorescent Semiconductor Nanocrystals and their Application to Biological Labeling (2001) Single Molecules 2, 261-276.

Alivisatos, P. The use of nanocrystals in biological detection. (2004) Nature Biotechnology 22, 47-52.

Peng et al. Epitaxial Growth of Highly Luminescent CdSe/CdS Core/Shell Nanocrystals with Photostability and Electronic Accessibility. (1997) Journal of the American Chemical Society 119, 7019-7029.

Hines, M. A., Guyot-Sionnest, P. Synthesis and Characterization of Strongly Luminescing ZnS-Capped CdSe Nanocrystals. (1996) Journal of Physical Chemistry. 100, 468-471.

Dabbousi et al. (CdSe) ZnS Core-Shell Quantum Dots: Synthesis and Characterization of a Size Series of Highly Luminescent Nanocrystallites. (1997) Journal of Physical Chemistry B 101, 9463-9475.

Tsay et al. Hybrid Approach to the Synthesis of Highly Luminescent CdTe/ZnS and CdHgTe/ZnS Nanocrystals (2004) Journal of the American Chemical Society 126, 1926-1927.

Bruchez et al. Semiconductor Nanocrystals as Fluorescent Biological Labels. (1998) Science 281, 2013-2016.

Gerion et al. Synthesis and Properties of Biocompatible Water-Soluble Silica-Coated CdSe/ZnS Semiconductor Quantum Dots. (2001) Journal of Physical Chemistry B 105, 8861-8871.

Chan, W. C. W., Nie, S. M. Quantum Dot Bioconjugates for Ultrasensitive Nonisotopic Detection. (1998) Science 281, 2016-2018.

Guo et al. Luminescent CdSe/CdS Core/Shell Nanocrystals in Dendron Boxes: Superior Chemical, Photochemical and Thermal Stability. (2003) J Am Chem Soc 125, 3901-9.

Larson et al. Water-Soluble Quantum Dots for Multiphoton Fluorescence Imaging in Vivo. (2003) Science 300, 1434-6.

Dubertret et al. In Vivo Imaging of Quantum Dots Encapsulated in Phospholipid Micelles. (2002) Science 298, 1759-62.

Mattoussi et al. Bioconjugation of Highly Luminescent Colloidal CdSe-ZnS Quantum Dots with an Engineered Two-Domain Recombinant Protein. (2001) Physica Status Solidi B-Basic Research 224, 277-283.

Kim, S., Bawendi, M. G. Oligomeric Ligands for Luminescent and Stable Nanocrystal Quantum Dots. (2003) J Am Chem Soc 125, 14652-3.

Pinaud et al. Bioactivation and Cell Targeting of Semiconductor CdSe/ZnS Nanocrystals with Phytochelatin-Related Peptides. (2004) J. Am. Chem. Soc. 126, 6115-6123.

Manna et al. Epitaxial Growth and Photochemical Annealing of Graded CdS/ZnS Shells on Colloidal CdSe Nanorods (2002) Journal of the American Chemical Society. 124, 7136-7145.

Murray et al. Synthesis and Characterization of Nearly Monodisperse CdE (E = S, Se, Te) Semiconductor Nanocrystallites. (1993) Journal of the American Chemical Society 115, 8706-8715.

Peng, Z. A., Peng, X. G. Nearly Monodisperse and Shape-Controlled CdSe Nanocrystals via Alternative Routes: Nucleation and Growth. (2002) Journal of the American Chemical Society 124, 3343-3353.

Li et al. Large-Scale Synthesis of Nearly Monodisperse CdSe/CdS Core/Shell Nanocrystals Using Air-Stable Reagents via Successive Ion Layer Adsorption and Reaction (2003) Journal of the American Chemical Society 125, 12567-12575.

Talapin et al. Highly Luminescent Monodisperse CdSe and CdSe/ZnS Nanocrystals Synthesized in a Hexadecylamine Trioctylphosphine OxideTrioctylphospine Mixture. (2001) Nano Letters 1, 207-211.

Magde et al. Fluorescence Correlation Spectroscopy. 11. An Experimental Realization. (1974) Biopolymers 13, 29-61.

Rigler et al. (1993) European Biophysics Journal 22, 169-175.

Ebenstein et al. Fluorescence quantum yield of CdSeOZnS nanocrystals investigated by correlated atomic-force and single-particle fluorescence microscopy. (2002) Applied Physics Letters 80, 4033-4035.

Åkerman et al., "Nanocrystal Targeting in Vivo", PNAS vol. 99 No. 20, Oct. 1, 2002 (pp. 12617-12621).

www.qdots.com/new/technology, Quantum Dot Corporation, Oct. 21, 2003 (15 pages).

Barchi, JJ., Svarosky, S., "Glyconanotechnology: Construction and Properties of Sugar/Peptide-Bearing Nanoparticles", slide presentation Boston, MA, May 5, 2003 (19 pages).

Chan et al., "Luminescent Quantum Dots for Multiplexed Biological Detection and Imaging", Current Opinion in Biotechnology 2002, vol. 13, Elsevier Science, Ltd. (pp. 40-46).

Wang et al., "Stabilization of Inorganic Nanocrystals by Organic Dendrons", J. Am. Chem. Soc. vol. 124, No. 10, Feb. 14, 2002 (pp. 2293-2298).

Chan, "Quantum Dot Bioconjugates for Ultrasensitive Nonisotopic Detection", Science, vol. 281, Sep. 25, 1998 (pp. 2016-2018).

Wu et al., "Immunofluorescent Labeling of Cancer Marker Her2 and Other Cellular Targets with Semiconductor Quantum Dots", Nature Biotechnology, vol. 21, Jan. 2003 (pp. 41-46).

Liang et al., "Functionalized CdSe quantum dots as selective silver ion chemodosimeter", Analyst, 129(7), Jul. 2004, pp. 619-622.

(Search 3) Results of Lexis search performed Sep. 2004. Search string = (quantum dot or quantum confin! or nanocrystal!) and bio! and (mercapto! or thio!).

Chen, "Synthesis of Glyconanospheres Containing Luminescent CdSe-ZnS Quantum Dots", Nano Letters, vol. 3, No. 5, 2003 (pp. 581-584).

Communication of Aug. 25, 2008 in European Patent Application No. EP 03 799 767.3-2107.

Office Action mailed Dec. 28, 2009 in U.S. Appl. No. 10/513,567.

Office Action mailed Apr. 2, 2009 in U.S. Appl. No. 10/513,567.

G. Iyer et al., "Solubilization of Quantum Dots with a Recombinant Peptide from *Escherichia coli*", Small, 3(5) (2007) 793-798.

X. Michalet et al., "Quantum dots for live cells, in vivo imaging, and diagnostics", Science, 307 (2005) 538-544.

X.Michalet et al., "The power and prospects of fluorescence microscopies and spectroscopies", Annu. Rev. Biophys. Biomol. Struct., 32 (2003) 161-182.

F.Pinaud et al., "Advances in fluorescence imaging with quantum dot bio-probes", Biomaterials, 27 (2006) 1679-1687.

Hammes et al., Methylation of (2-Methylethanethiol-bis-3,5-dimethylpyrazolyl)methane Zinc Complexes and Coordination of the Resulting Thioether: Relevance to Zinc-Containing Alkyl Transfer Enzymes., *Inorg. Chem.* 40 (2001) 919-927.

Tobin et al., "Structural Characterization of the Zinc Site in Protein Farnesyltransferase", *J. Am. Chem. Soc.* 125(33) (2003) 9962-9969.

Myers et al., "Metal-coordination sphere in the methylated Ada protein-DNA co-complex", Chemistry & Biology 1(2) (1994) 91-97.

Huang et al., "Evidence for a Catalytic Role of Zinc in Protein Farnesyltransferase", Journal of Biological Chemistry, 272(1) (Jan. 13, 1997) 20-23.

Vahrenkamp, H., "Transitions, Transition States, Transition State Analogues:Zinc Pyrazolylborate Chemistry Related to Zinc Enzymes", Acc. Chem. Res. 32 (1999) 589-596.

Kyte, J. et al., "A Simple Method for Displaying the Hydropathic Character of a Protein", J. Mol. Biol. 157 (1982) 105-132.

Pinaud et al., "Supporting information for Bioactivation and Cell Targeting of Semiconductor CdSe/ZnS Nanocrystals with Phytochelatin-related Peptides", S-1-S-11, published online (Web) at http://pubs.acs.org/doi/suppl/10.1021/ja031691c (file http://pubs.acs.org/doi/suppl/10.1021/ja031691c/suppl_file/ja031691csi20040223_054743.pdf) on Apr. 22, 2004, together with Pinaud et al., "Bioactivation and Cell Targeting of Semiconductor CdSe/ZnS Nanocyrstals with Phytochelatin-Related Peptides", J. Am. Chem. Soc., 126(19) (2004) 6115-6123.

Examiner Interview Summary Record mailed Mar. 26, 2010 in U.S. Appl. No. 10/513,567.

Pinaud et al., "Supporting information for Bioactivation and Cell Targeting of Semiconductor CdSe/ZnS Nanocrystals with Phytochelatin-related Peptides", S-1-S-11, published online (Web) at http://pubs.acs.org/doi/suppl/10.1021/ja031691c (file http://pubs.acs.org/doi/suppl/10.1021/ja031691c/suppl_file/ja031691csi20040223_054948.pdf) on Apr. 22, 2004, together with Pinaud et al., "Bioactivation and Cell Targeting of Semiconductor CdSe/ZnS Nanocyrstals with Phytochelatin-Related Peptides", J. Am. Chem. Soc., 126(19) (2004) 6115-6123.

U.S. Patent and Trademark Office Interview Summary dated Jul. 7, 2009 for U.S. Appl. No. 11/630,584.

U.S. Patent and Trademark Office Action dated Apr. 2, 2009 for U.S. Appl. No. 11/630,584.

U.S. Patent and Trademark Office Interview Summary dated Dec. 23, 2010 for U.S. Appl. No. 11/630,584.

U.S. Patent and Trademark Office Notice of Allowance dated Apr. 5, 2010 for U.S. Appl. No. 11/630,584.

U.S. Patent and Trademark Office Notice of Allowance dated Dec. 23, 2010 for U.S. Appl. No. 11/630,584.

* cited by examiner

SEQUENCE LISTING

```
<160> NUMBER OF SEQ ID NOS: 8

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (1)
<223> OTHER INFORMATION: Cha
<220> FEATURE:
<221> NAME/KEY: MOD_RES
<222> LOCATION: (4)
<223> OTHER INFORMATION: Cha
<220> FEATURE:
<221> NAME/KEY: MOD_RES
<222> LOCATION: (7)
<223> OTHER INFORMATION: Cha
<220> FEATURE:
<221> NAME/KEY: MOD_RES
<222> LOCATION: (10)
<223> OTHER INFORMATION: Cha

<400> SEQUENCE: 1

Xaa Cys Cys Xaa Cys Cys Xaa Cys Cys Xaa
 1               5                  10

<210> SEQ ID NO 2
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (11)
<223> OTHER INFORMATION: Cha
<220> FEATURE:
<221> NAME/KEY: MOD_RES
<222> LOCATION: (14)
<223> OTHER INFORMATION: Cha
<220> FEATURE:
<221> NAME/KEY: MOD_RES
<222> LOCATION: (17)
<223> OTHER INFORMATION: Cha
<220> FEATURE:
<221> NAME/KEY: MOD_RES
<222> LOCATION: (20)
<223> OTHER INFORMATION: Cha

<400> SEQUENCE: 2

Gly Ser Glu Ser Gly Gly Ser Glu Ser Gly Xaa Cys Cys Xaa Cys Cys
 1               5                  10                  15

Xaa Cys Cys Xaa
        20
```

```
<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (11)
<223> OTHER INFORMATION: Cha
<220> FEATURE:
<221> NAME/KEY: MOD_RES
<222> LOCATION: (14)
<223> OTHER INFORMATION: Cha
<220> FEATURE:
<221> NAME/KEY: MOD_RES
<222> LOCATION: (17)
<223> OTHER INFORMATION: Cha
<220> FEATURE:
<221> NAME/KEY: MOD_RES
<222> LOCATION: (20)
<223> OTHER INFORMATION: Cha

<400> SEQUENCE: 3

Gly Ser Ser Ser Gly Gly Ser Ser Ser Gly Xaa Cys Cys Xaa Cys Cys
  1               5                  10                  15

Xaa Cys Cys Xaa
            20

<210> SEQ ID NO 4
<211> LENGTH: 29
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (20)
<223> OTHER INFORMATION: Cha
<220> FEATURE:
<221> NAME/KEY: MOD_RES
<222> LOCATION: (23)
<223> OTHER INFORMATION: Cha
<220> FEATURE:
<221> NAME/KEY: MOD_RES
<222> LOCATION: (26)
<223> OTHER INFORMATION: Cha
<220> FEATURE:
<221> NAME/KEY: MOD_RES
<222> LOCATION: (29)
<223> OTHER INFORMATION: Cha

<400> SEQUENCE: 4

Gly Pro Lys Lys Lys Arg Lys Val Gly Gly Ser Glu Ser Gly Gly Ser
  1               5                  10                  15

Glu Ser Gly Xaa Cys Cys Xaa Cys Cys Xaa Cys Cys Xaa
            20                  25

<210> SEQ ID NO 5
<211> LENGTH: 21
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (12)
<223> OTHER INFORMATION: Cha
```

```
<220> FEATURE:
<221> NAME/KEY: MOD_RES
<222> LOCATION: (15)
<223> OTHER INFORMATION: Cha
<220> FEATURE:
<221> NAME/KEY: MOD_RES
<222> LOCATION: (18)
<223> OTHER INFORMATION: Cha
<220> FEATURE:
<221> NAME/KEY: MOD_RES
<222> LOCATION: (21)
<223> OTHER INFORMATION: Cha

<400> SEQUENCE: 5

Lys Gly Ser Glu Ser Gly Gly Ser Glu Ser Gly Xaa Cys Cys Xaa Cys
 1               5                  10                  15

Cys Xaa Cys Cys Xaa
            20

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Gly Ser Glu Ser Gly Gly Ser Glu Ser Gly
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Gly Ser Ser Ser Gly Gly Ser Ser Ser Gly
 1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MOD_RES
<222> LOCATION: (1)
<223> OTHER INFORMATION: Ala substituted with a hydrophobic group
<220> FEATURE:
<221> NAME/KEY: MOD_RES
<222> LOCATION: (4)
<223> OTHER INFORMATION: Ala substituted with a hydrophobic group
<220> FEATURE:
<221> NAME/KEY: MOD_RES
<222> LOCATION: (7)
<223> OTHER INFORMATION: Ala substituted with a hydrophobic group
<220> FEATURE:
<221> NAME/KEY: MOD_RES
<222> LOCATION: (10)
<223> OTHER INFORMATION: Ala substituted with a hydrophobic group

<400> SEQUENCE: 8

Ala Cys Cys Ala Cys Cys Ala Cys Cys Ala
 1               5                  10
```

PEPTIDE-COATED NANOPARTICLES WITH GRADED SHELL COMPOSITIONS

This application is a Continuation Application of U.S. patent application Ser. No. 11/630,5846, filed Dec. 22, 2006, which is a National Stage of International Application Number PCT/US2005/022102, filed Jun. 20, 2005, which claims the benefit of U.S. Provisional Application Number 60/581,828, filed Jun. 22, 2004. This invention was made with Government support under United States National Institutes of Health Grant No. EB000312, and United States National Institutes of Health Grant No. RR014891. The United States Government has certain rights in this invention.

BACKGROUND OF THE INVENTION

1. Field of the Invention

The present invention relates generally to nanoparticles that are composed of a nanocrystal core surrounded by a shell of semiconductor molecules wherein the surface of the shell is coated with a bioactivation peptide. More particularly, the present invention is directed to improving the photoluminescence and quantum yield of such peptide-coated nanoparticles.

2. Description of Related Art

The publications and other reference materials referred to herein to describe the background of the invention and to provide additional detail regarding its practice are hereby incorporated by reference. For convenience, the reference materials are numerically referenced and grouped in the appended bibliography. The contents of the publications and other reference materials are hereby incorporated by reference.

Core/shell nanocrystals (NCs) such as CdSe/ZnS are nanometer scale inorganic clusters of semiconductor material useful for fluorescent labeling in multicolor biological imaging and detection (1, 2). These colloidal NCs consist of an inorganic particle and an organic coating that determines their solubility, functionality, and influences their photophysics. In order for these NCs to be biocompatible, they must be water-soluble, nontoxic to the cell, and offer conjugation chemistries for attaching recognition molecules to their surfaces. In addition they should efficiently target to biomolecules of interest, be chemically stable, and preserve their high photostability. The requirements for their application in single-molecule biological studies are even more stringent: fluorescent NCs should be monodisperse, have relatively small size (to limit steric hindrance), reduced blinking, large saturation intensity and high photoluminescence quantum yield (QY).

Two coating steps are necessary to render CdSe NCs synthesized in organic solvents highly luminescent, water-soluble, and biocompatible. The first coating step is the chemical deposition of higher band gap inorganic shells over NC cores (3-6). These shells serve as isolation layers, protecting the exciton wavefunction from nonradiative recombination processes at surface traps. The second coating step utilizes ligand exchange to functionalize the NCs. Various coating chemistries have been described: silanization (7, 8), mercaptoalkanoic acid ligands (9), organic dendrons (10), amphiphilic polymers (11), phospholipid micelles (12), recombinant proteins (13), and oligomeric phosphines (14). The fact that several different coatings have continuously been introduced points to the difficulty in achieving all desired properties with one universal coating. It implies that different coatings will most likely be necessary for various applications. NCs with thicker coatings will tend to have better photostabilities and higher quantum yields whereas smaller NCs with thin coatings may be less photostable but should be better suited as intracellular probes.

As set forth in PCT US2003/014401, ligand exchange of nanopartilces, such as CdSe/ZnS core/shell NCs, with phytochelatin-related peptides was found to provide bioactive NCs with only a thin water-soluble shell (15). Peptide coating endows the NCs with exceptional colloidal properties as proven by HPLC, gel electrophoresis, atomic force microscopy (AFM), transmission electron microscopy (TEM), and fluorescence antibunching studies (16). These peptides have a C-terminal adhesive hydrophobic domain with multiple cysteinyl thiolate binding sites and a hydrophilic domain that gives the NCs their desired solubility and functionality. However, this previously reported biofunctionalization scheme significantly reduces the QY of CdSe/ZnS NCs in aqueous buffer.

SUMMARY OF THE INVENTION

In accordance with the present invention, the composition and structure of inorganic shells grown over CdSe semiconductor nanocrystal dots and rods have been optimized by grading to yield enhanced photoluminescence properties after coating with phytochelatin-related peptides. It was discovered that in addition to the peptides imparting superior colloidal properties and providing biofunctionality in a single step reaction, the graded shells and optional pre-treatment with UV irradiation resulted in high quantum yields (10-35%) for the nanocrystals in water. Moreover, peptide coating leads to a noticeable red-shift in the absorption and emission spectra for graded CdS/ZnS shells, suggesting that exciton-molecular orbital (X-MO) coupling might take place in these hybrid inorganic-organic composite materials.

Peptide-coated nanoparticles in accordance with the present invention include a nanocrystal core surrounded by a shell wherein said shell comprises a graded mixture of at least two different semiconductor molecules to provide a graded shell. The graded shell is coated with at least one bioactivation peptide to render the nanoparticles biocompatible. The peptide-coated nanoparticles having graded shells were found to have QY's that were unexpectedly higher than the QY of peptide-coated nanoparticles having non-graded shells.

As another feature of the present invention, the nanocrystal core/graded shell nanoparticles are optionally subjected to UV irradiation and/or laser annealing prior to and after the addition of the peptide coating. Such laser annealing and/or UV radiation provides an additional increase in the QY of the peptide-coated nanoparticles.

The above-described and many other features and attendant advantages of the present invention will become better understood with reference to the following detailed description.

DETAILED DESCRIPTION OF THE INVENTION

The present invention is based in part on the invention(s) described in PCT 2003/014401 (International Publication No. WO 2004/039830 A2) which is owned by the same assignee as the present invention. PCT 2003/014401 describes converting particles that are biologically non-functional into bioactivated particles that have one or more functional characteristics that are necessary to make the particles useful in biological systems. This is accomplished by attaching bioactivation peptides (as described in detail below) to the surface of the particles. These specialized peptides are capable of imparting one or more biologically important functions to the particles. The use of these "bioactivation peptides" effectively eliminates the need for conventional linking agents that have been used in the past to connect biologically functional groups to particle surfaces. In addition, the use of bioactivation peptides to impart biological function(s) to particles is extremely versatile and relatively simple. It has wide applications to any type of biological system where particles having specific biological functions are required.

The term "bioactivated particle" is intended to mean any particle that has been treated with bioactivation peptides so that the particle has one or more biological functions that it otherwise would not have. Examples of the types of functions that can be imparted to particles using bioactivation peptides include solubility in aqueous mediums, bioconjugation, targeting, therapy, imaging, detection, recognition and diagnosis.

The present invention is directed to nanoparticles that have been coated with bioactivation peptides where the nanoparticle is composed of a crystalline semiconductor core that is coated with a shell of a second semiconductor (core/shell nanoparticle). For the purposes of this specification, both nanocrystal dots and nanorods are considered to be nanoparticles. The bioactivation peptides are attached to the outer semiconductor shell. It was discovered that certain properties of these core/shell nanoparticles are enhanced when the shell is formed as a graded mixture of semiconductor molecules. These "graded" shells provide increased quantum yields as compared to core/shell nanoparticles where the shell is composed of one or more layers that are not graded. In addition, it was discovered that annealing of the core/graded shell nanoparticles with UV radiation (prior to and/or after coating with the bioactivation peptide) also improved quantum yields.

The core/graded shell nanoparticles of the present invention are coated with one or more bioactivation peptides. The bioactivation peptides include a molecular recognition part (MRP), which is also referred to herein as the surface recognition part (SRP). The SRP is the portion of the bioactivation peptide that attaches to the graded shell. The bioactivation peptide further includes a functional part that is located at one or both ends of the SRP. The functional part is made up of one or more functional agents that impart one or more biological functions to the particle.

The SRP is made up of binding clusters (BC's) and hydrophobic spacers (HS's). As few as one binding cluster and one hydrophobic spacer may be used to form the SRP. However, it is preferred that at least two or more BC's and HS's be used. The SRP/MRP includes three BC's and four HS's that alternate sequentially along the SRP. As is the case in any amino acid sequence, the SRP has an amino end and a carboxy end. Although it is preferred that a HS be located between each BC, it is not necessary. SRP's are possible where BC's and HS's are grouped together. The number of BC's and HS's that are needed to bind the bioreactive peptide to the surface of the graded shell will vary depending upon a number of parameters including the number of functional agents present in the functional part and the chemical characteristics of the functional agents. In addition, the type of particle surface as well as the particular amino acids used in the SRP must be taken into consideration. The particular number and types of BC's and HS's, as well as their orientation, can be determined by routine experimentation for each different type of particle and functional part.

The BC's are made up of one or more natural or unnatural amino acids or amino acid derivatives that are capable of binding to the particle surface. Exemplary amino acids include cysteine, methionine, histidine and derivatives thereof. The derivatives may be natural or unnatural. Exemplary amino acid derivatives include 3,3-diphenyl-Ala-OH, 2-amino-3,3-dimethylbutyric acid, (Also see http://www.sigmaaldrich.com/img/assets/6040/chemFiles_v1n5_unnaturalaa_small.pdf). The BC preferably includes two amino acids or derivatives and may include as many as 10 amino acids or derivatives. The particular amino acids or derivatives that are used to form the SRP may be the same or different. The make-up of the BC's for any given SRP will vary depending upon the particular functional parts being used and the intended particular particle surface for attachment. The BC make-up can be determined by routine experimentation once the particle to be bioactivated has been selected and the functional agent(s) has been chosen.

The HS's are composed of a compound that is hydrophobic and capable of binding with the BC's. Although any number of hydrophobic compounds can be used, it is preferred that the HS's include one or more natural or unnatural amino acids or derivatives that have been modified to be hydrophobic. Exemplary modified amino acids include hydrophobic alanine, hydrophobic glycine, hydrophobic isoleucine, hydrophobic leucine, hydrophobic methionine, hydrophobic arginine, hydrophobic valine, hydrophobic tryptophan and derivatives thereof. The preferred modification is to substitute a cyclohexyl group into the amino acid in place of H from the methyl group. Other hydrophobic groups, such as benzene, may be used in place of cyclohexyl. It is preferred that the HS contain a single hydrophobic amino acid. However, up to 10 hydrophobic amino acids may be present in any one HS.

The functional part (FP) of the bioactivation peptide includes functional agents attached to either the amino end of the SRP, the carboxy end of the SRP or both. The functional agent may be anything that is intended to impart a biological function to the particle. Exemplary functional agents include solubility agents, conjugation agents, targeting agents, therapeutic agents, imaging agents, detection agents, recognition agents and diagnostic agents. There may be some overlap in agents since some compounds may serve a dual purpose. The functional agent must be able to bind to the SRP or one of the other agents. The functional part may contain as few as one functional agent, such as a solubility agent, attached to only one end of the SRP. At the other extreme, two, three or more functional agents can be attached to one or both ends of the SRP.

For bioactivation peptides that are used to treat core/graded shell nanoparticles that are not soluble in aqueous media, it is preferred that a solubility agent be included in the functional part as a minimum. Although the solubility agent may be located anywhere, it is preferred that it is attached directly to one or both ends of the SRP. An exemplary solubility agent is a hydrophilic peptide that has from 1 to 100 amino acids. Specific examples include gly-ser-glu-ser-gly-gly-ser-glu-ser-gly (SEQ. ID. NO. 6), gly-ser-ser-ser-gly-gly-ser-ser-ser-gly (SEQ. ID. NO. 7). Numerous other hydrophilic peptides are possible. The solubility agent may also be other known hydrophilic compounds that can be attached to the SRP or a bioconjugation agent. Exemplary other solubility agents include polyethylene glycol, poly(ethylene oxide), polyelectrolytes and sugars. Sugars, such as cellobiose, sucrose and sialic acid are suitable. Exemplary polyelectrolytes include polyethylene immine.

The following is a list of various functional agents, other than solubility agents, that is intended to be exemplary only. As will be appreciated numerous other functional agents may be attached to the SRP to form bioactivation peptides that are suitable for coating the core/graded shell nanoparticles in accordance with the present invention:

Conjugation agents: biotin, avidin, streptavidin and derivatives, lysine, cysteine, asp artic acid, glutamic acid-terminated peptides (with reactive groups amines, thyoles, carboxyl, unnaturals, keto).

Targeting agents: antibodies, enzyme substrate, receptor ligands.

Therapeutic agents: taxol, herceptin.

Imaging agents: Fluorescin, bromophenyl blue, Iodine, Yttrium, Tritium, Metallotexaphyrins, many radioactive reagents, MR1 enhancing reagents, PET, CT, etc.

Detection agents: the same or similar to the above-listed imaging agents.

Recognition agents: same imaging/therapeutics conjugated to antibodies and/or recognition peptides.

Diagnostic agents: any of the above listed agents may be used as a diagnostic agent.

Demonstrative examples of bioactivation peptides that are suitable for coating the core/graded shell nanoparticles in accordance with the present invention are listed as follows:

Bioactivation Peptides with Solubility/Conjugation Agents:

(amide or acetyl)—MRP—hydrophilic peptide—biotin or avidin/streptavidin biotin—hydrophilic peptide—MRP carboxamide biotin—MRP—carboxamide carboxamide-MRP-hydrophilic peptide-NHS ester carboxamide-MRP-hydrophilic peptide-keto group DNA oligo—hydrophilic peptide—MRP carboxamide keto, thiols will allow orthogonal conjugation to different peptides (on the same nanoparticles or on different particles in the same suspension).

Bioactivation Peptides with Solubility/Tumor Targeting Agents:

(amide or acetyl)—MRP hydrophilic peptide—transferrin (or an antibody to one of the tumor receptors transferrin—hydrophilic peptide—MRP—carboxamide tumor targeting sequence—hydrophilic peptide—MRP—carboxamide DNA oligo—hydrophilic peptide—MRP carboxamide transferrin—hydrophilic peptide—MRP hydrophillic peptide—tranferrin Other agents include antibody, minibody, single chain fragment.

Bioactivation Peptides with Solubility Agents:

Amide or acetyl—MRP—hydrophilic peptide hydrophilic peptide—MRP—carboxyl hydrophilic peptide—MRP—carboxamide succinyl-hydrophilic peptide—MRP carboxamide hydrophilic peptide—MRP—hydrophilic peptide PEG—hydrophilic peptide—MRP—carboxamide PEG—MRP—hydrophilic peptide Other exemplary functional agents include 1,4,7,10-tetraazacyclodoecane-1,4,7,10-tetraacetic acid (DOTA), Ni-NTA, I, Yt, C as well as many types of chelators, metallic ions, isotopes, and magnetic materials.

The MRP of the bioactivation peptides may be made by simple peptide synthesis protocols that are well established. The various functional agents are attached to the MRP or other functional agent by peptide synthesis or known conjugation techniques for the particular agent. The bioactivation peptides may be completely synthesized with all of its functional agents being attached prior to mixing with core/graded shell nanoparticles. Alternately, a bioactivation peptide may be attached to the surface of the graded shell with only part of the total intended functional agents attached.

The preceding single and multiple step synthesis protocols are exemplary only with it being understood that the same basic procedures may be used to produce bioactivated particles having many more functional agents attached to one or both ends the MRP. In many situations, it is desirable to attach different bioactivation peptides to the same core/graded shell nanoparticle. Each of the bioactivation peptides may carry a single different functional agent or they may each have multiple functional agents. The following examples demonstrate some of the many different types of bioactivation peptides that can be coated onto the graded shell of nanoparticles in accordance with the present invention.

Bioactivation peptides, which are suitable for attachment to the graded shells, have the formula:

A-[Ala-C-C-Ala-C-C-Ala-C-C-Ala]-B where the central sequence shown in brackets is the SRP (MRP) and A and B are the functional parts. A and B are either the same or different and independently comprise a polypeptide group, an acetyl group, an amine group, a carboxamide group or a biotin group, Ala is alanine substituted with a hydrophobic group, and C is cysteine. Preferred hydrophobic groups are cyclohexyl groups, thus a preferred bioactivation peptide coating for the graded shells have the sequence Cha-C-C-Cha-C-C-Cha-C-C-Cha (SEQ. ID. NO. 1), where Cha is cyclohexyl alanine.

The bioactivation peptides are applied directly to the graded shell of the nanoparticle without the use of a separate linking agent. The bioactivation peptide gives the particles molecular recognition capabilities and water/buffer solubility. The particles can be conjugated to other molecules and can be given other desired properties by the large diversity offered by amino acids (hydrophobic/hydrophilic interactions and ionic/charge interactions). The invention is useful for NCs fluorescent probe targeting, targeting of particles to body parts (tumors) for x-ray medical imaging (x-ray of element specific core level and possibly others) and for x-ray photodynamic/photothermal therapy (delivering free radicals/heat to element specific core level via absorption of monochromatic x-ray).

The bioactivation peptides also allow self-assembly of organic-inorganic nanostructure hybrids by molecular recognition. They allow interfacing enzymes, biocatalysts and other proteins/RNA catalysts with nanoparticles to produce nano-machines/molecular machines that can be activated by light and/or charge. For example, charge generated by light in the nanoparticle can be separated and transferred to the protein to trigger enzymatic reaction, catalysis etc. (yielding, for example, light activated/triggered therapeutics.

In accordance with the present invention, the bioactivation peptides are coated onto the surface of a particle that includes a nanocrystal core surrounded by a shell that comprises a graded mixture of at least two different semiconductor molecules. The term "nanocrystal core" is intended to cover both nanocrystal dot and nanonocrytal rods. The nanocrystal core is preferably a single crystal particle having an average cross-section no larger than about 20 nanometers (nm) or $20\times10^{-9}$ meters (200 Angstroms), preferably no larger than about 10 nm (100 Angstroms) and a minimum average cross-section of about 1 nm. Nanocrystal cores on the order of 4 to 6 nm are particularly preferred. Nanorods may also serve as the nanocrystal core. Typical dimensions for suitable nanorods are 1 to 10 nm diameter with a length of 5 to 100 nm. Nanorods having a diameter of around 5 nm and a length of 25 nm are preferred.

The material used to form the nanocrystal core can be a nanometer crystal or nanocrystal of Group II-VI and/or Group III-V semiconductor compounds capable of emitting electromagnetic radiation upon excitation, although the use of Group IV semiconductors such as germanium or silicon, or the use of organic semiconductors, may be feasible under certain conditions.

Examples of nanocrystals of Group II-VI semiconductors which are suitable for used as nanocrytal cores are as follows: MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof. Examples of suitable nanocrystals of Group III-V semiconductors are: GaAs, InGaAs, InP, and InAs and mixed compositions thereof. As mentioned above, the use of Group IV semiconductors such as germanium or silicon, or the use of organic semiconductors, may also be feasible under certain conditions. The semiconductor nanocrystals may also include alloys comprising two or more semiconductors selected from the group consisting of the above Group III-V compounds, Group II-VI compounds, Group IV elements, and combinations thereof. CdSe is a preferred nanocrystal core.

Formation of nanometer crystals of Group III-V semiconductors is described in Alivisatos et al. U.S. Pat. No. 5,751, 018; Alivisatos et al. U.S. Pat. No. 5,505,928; and Alivisatos et al. U.S. Pat. No. 5,262,357, which also describes the formation of Group II-VI semiconductor nanocrystals, and which is also assigned to the assignee of this invention. Also described therein is the control of the size of the semiconductor nanocrystals during formation using crystal growth terminators. The teachings of Alivisatos et al. U.S. Pat. No. 5,751, 018, and Alivisatos et al. U.S. Pat. No. 5,262,357 are each hereby specifically incorporated by reference.

The nanocrystal core is surrounded by a thin shell of semiconductor molecules. As a feature of the present invention, the shell is a "graded shell" that is made up of at least two different semiconductor molecules. The term "graded shell" is used to describe a shellthat includes at least two different semiconductor molecules wherein the compostion of the shell over its radial dimension progresses gradually from one semiconductor to the other. The preparation of graded shells is described in United States Published Pat. Appl. No. 2005/0054004. The typical procedure for preparing graded shells inyloves exposing the nanocrystal core to one of the semiconductor precursor and then slowing adding additional semiconductor(s) in amounts that are selected to provide a gradual grading of the shell composition from one semiconductor to the other(s) across the radial dimension of the shell. The semiconductor molecules may be chosen from the same groups of semiconductors set for above. Exemplary semiconductor molecules include ZnS, CdS, ZnSe and CdSe. Graded Shells that are composed of a mixture of ZnS and CdS molecules are preferred. Other possible components of mixtures including the aforementioned molecules are ZnTe, CdTe. All II-VI, and III-V materials may be possibly incorporated into graded shells.

For graded shells composed of two different semiconductor molecules, the total amount of each semiconductor present in the graded shell may vary from 5 to 95 percent of the total molecules in the shell. It is preferred that the amount of each semiconductor be at least 15 percent of the total molecules in the shell. In a preferred embodiment, the number of CdS is 20 percent of the shell and ZnS is 80% When more than two types of semiconductor molecules are used to form the shell, the relative amounts can be varied widely provided that each type of semiconductor molecule makes up at least 5 percent of the total number of molecules in the shell.

The graded shell is preferably made up of from 1-10 layers of graded semiconductor molecules where each of the layers is one molecule thick. These layers that are a single molecule thick are referred to as monomolecular layers or simply "monolayers". Shells that contain from 4 to 6 monolayers of graded semiconductors are particularly preferred. The graded shell is formed in the same manner as known procedures for forming shells that contain a single semiconductor (See 3 and 4). In these procedures, the nanocrystal cores are exposed to one semiconductor precursor at a time to form a shell having monolayers composed of single semiconductors. In contrast, the present invention requires that the nanocrystal core be exposed in a graded manner to two or more different semiconductor precursors so as to form monolayers that progress in composition gradually from one semiconductor to another across the radial dimension of the shell. The relative amounts of different semiconductors present in each monolayer is controlled by solvents used, coordinating ligands, temperature and varying the amount of semiconductor precursor in the solution to provide the desired grading in composition radially across the shell A non-limiting example of the MRP for a suitable bioactivation peptide is Cha-C-C-Cha-C-C-Cha-C-C-Cha (SEQ. ID. NO. 1) with Cha standing for Cyclohexyl alanine and C for cysteine. It is not required that the alanine to be substituted with a cyclohexyl group; however, cyclohexyl groups are preferred. The peptide can be synthesized using N-Boc or F-moc protecting groups and sequences may be N-acetylated and/or C-carboxylated. The bioactivation peptides coated onto the graded shell of the nanoparticles by simple addition of the bioactivation peptides to nanocrystal core/graded shell nanoparticles and allowed to form a good dispersion of the nanoparticles in DMSO which subsequently yield stable and highly monodisperse dilutions of the nanocrystals in water and buffer. Stability in water and buffers is enhanced by the addition of a hydrophilic sequence at the N-terminus of the Cha-C-C-Cha . . . sequence. The following sequence may be used: G-S-E-S-G-G-SE-S-G-Cha-C—C-Cha-C-C-Cha-C-C-Cha (SEQ. ID. NO. 2).

Various sequences of different length may be attached on the surface of the graded shell with the same Cha-C-C-Cha-C-C-Cha-C-C-Cha MRP sequence being present. Table 1 sets forth examples of various bioactivation peptide sequences that can be used to solubilize the nanocrystal core/graded shell nanoparticles.

TABLE 1

| Name | Sequence |
|---|---|
| ChaCha | NH2-Cha-C-C-Cha-C-C-Cha-C-C-Cha-Carboxamide (SEQ. ID. NO. 1) |
| ChaCha acetylated | acetylated-Cha-C-C-Cha-C-C-Cha-C-C-Cha-Carboxamide |
| ChaCha E swimmer | NH2-G-S-E-S-G-G-S-E-S-G-Cha-C-C-Cha-C-C-Cha-C-C-Cha-Carboxamide (SEQ. ID. NO. 2) |
| CH3 | acetylated-G-S-E-S-G-G-S-E-S-G-Cha-C-C-Cha-C-C-Cha-C-C-Cha-Carboxamide (SEQ. ID. NO. 2) |
| COOH | acetylated-G-S-S-S-G-G-S-S-S-G-Cha-C-C-Cha-C-C-Cha-C-C-Cha-Carboxamide (SEQ. ID. NO. 3) |
| NLS | acetylated-G-P-K-K-R-K-V-G-G-S-E-S-G-G-S-E-S-G-Cha-C-C-Cha-C-C-Cha-C-C-Cha-Carboxamide (SEQ. ID. NO. 4) |
| K swimmer | acetylated-K-G-S-E-S-G-G-S-E-S-G-Cha-C-C-Cha-C-C-Cha-C-C-Cha-Carboxamide (SEQ. ID. NO. 5) |
| Biotin | Biotin-Cha-C-C-Cha-C-C-Cha-C-C-Cha-Carboxamide |

Once soluble in water, the coated nanocrystal core/graded shell nanoparticles are usually purified from excess peptides. Purification can be done via dialysis techniques or ultrafiltration on membrane of given molecular weight cut off (MWCO).

The use of bioactivation peptides attached to nanocrystal core/graded shell nanoparticles not only provides water solubility and chemical handles, but also allows the control of the charge, and possibly other properties such as hydrophobicity, hydrophilicity, polarity, and reactivity. Simply by varying the bioactivation peptides, it is possible to engineer the nanoparticles and to dial in desired characteristics.

CdSe nanocrystal core/ZnS shell nanoparticles were initially chosen for investigation because the ZnS shell offers exceptional photostability for CdSe NCs. However, this shell tends to decrease the QY of CdSe NCs with increasing shell thickness because of large lattice mismatch (12%) (5). In order to decrease the lattice mismatch, Manna and coworkers grew CdS/ZnS graded shells over CdSe nanorods and demonstrated large increases in QY and high photostability after laser annealing (17).

We initially hypothesized that the possibility of growing larger shells with cadmium dopants would prevent the exciton from interacting with the environment, thus allowing higher quantum yield and less nonradiative relaxation. However, we show in the following examples that this shell may actually allow the exciton (X) to interact with the molecular orbitals (MOs) of the bioactivation peptides. By reducing the shell band gap offset, and/or by introducing low lying (mid gap) energy levels into the shell, the excitonic wavefunction can be made to leak further out of the core, affording such exciton-molecular orbital interactions (X-MO interactions). Such interactions can affect the NCs' photoluminescence more favorably than a higher bandgap shell (ZnS).

In order to characterize the effects of shell composition and structure as well as UV irradiation on the fluorescence of the nanoparticles as set forth in the following examples, we used ensemble UV/V is absorption and photoluminescence emission spectroscopy. Fluorescence correlation spectroscopy was also employed to study the nature of quantum yield increases of peptide coated NCs with UV irradiation.

Examples of Practice are as Follows:

Samples: Four different shell compositions were grown over spherical NC cores (Table 2). One of the shells was also grown over nanorods: (#1) 4-5 monolayers of ZnS shell grown over 4.5 nm CdSe cores (comparative example); (#2) 4-5 monolayers of CdS/ZnS graded shell grown over 4.5 nm CdSe cores (example in accordance with the invention); (#3) 2-3 monolayers of CdS followed by 2-3 monolayers of ZnS layered shells grown over 4.5 nm CdSe cores (comparative example); (#4) 5 monolayers of CdS shell grown over 3.5 nm CdSe cores (comparative example); and (#5) 4-5 monolayers of CdS/ZnS graded shell grown over ~5×25 nm CdSe nanorods (Example in accordance with the present invention).

Materials/Chemicals: Dimethylcadmium $(Cd(CH_3)_2$, 97%) and tri-n-butylphosphine (TBP, 99%) were purchased from Strem (Newburyport, Mass.). Cadmium oxide, diethylzinc ($C_4H_{10}Zn$, 1.0 M solution in heptane), and hexamethyldisilthiane ($C_6H_{18}Si_2S$ or $TMS_2S$) were purchased from Aldrich (Milwaukee, Wis.). Hexylphosphonic acid, tetradecylphosphonic acid, and trioctylphosphine oxide (TOPO, Tech) were purchased from Alfa Aesar (Ward Hill, Mass.). Peptides were purchased from Synpep with at least 80% purity.

CdSe quantum dot and nanorod core synthesis: Quantum dot cores were synthesized by using similar methods developed by Murray et al. (18). The precursor solution was prepared in a glovebox where selenium powder (0.149 g) and tributylphosphine (1.48 g) were mixed until the selenium dissolved. Dimethyl cadmium (0.36 g) as well as an additional amount of tributylphosphine (8 g) were added to the solution. In a 100 mL round-bottomed flask, TOPO (8 g, Technical grade) was heated to 120° C. under nitrogen flow. The flask was purged under vacuum for 30 minutes and 2 more times for 5 minutes each. The temperature was raised to 360° C. and 2.5 mL of the precursor solution was injected quickly. After injection, the temperature was quickly adjusted to 300° C. for growth. To increase the size of the NCs and prevent Ostwald ripening, additional injections of 1 mL of the stock solution were added every 30 minutes until the desired size was reached. The solution was cooled to 40° C. and methanol was used to precipitate the nanocrystals. Detailed procedures Nanorod cores were synthesized by using the two pot method with aged Cd-TDPA complexes established by Peng et al. (19).

Shell Synthesis: ZnS shells were grown over CdSe cores according to Hines et al. (4). with the following modifications. 10-40 mg of precipitated cores were redispersed in 0.5 ml of chloroform or toluene. A solution containing TBP (8.26 g), diethylzinc (1.26 g), hexamethyldisilithiane (0.304 g), and optionally dimethyl cadmium was prepared in a glove box and stored under nitrogen at -20° C. A solution of trioctylphosphine oxide (TOPO) (4 g, 99%) was heated to 100° C. and purged for 30 min under vacuum. This was repeated twice for 5 min intervals. Tributylphosphine (TBP) (0.5 ml) was injected into the TOPO solution. The core solution was also injected into the solution at 100° C. and purged in order to evaporate chloroform and toluene. The reaction flask was filled with nitrogen and heated to 160° C. with TBP. The shell solution was injected at ~0.1 mL/min. For formation of CdS/ZnS graded shells, the cadmium precursors were injected with the zinc precursors as follows to provide a grade shell that gradually progressed from ZnS to CdS molecules across the radial dimension of the shell. The total amounts of the semiconductors in the graded shell was approximately 20 percent CdS molecules and 80 percent ZnS molecules. Instead of using dimethyl cadmium, CdO may be reacted with trioctylphosphine (TOP) at 300° C. until a clear solution is produced, followed by the addition of the cores at 100° C., and subsequent injection of ZnS precursor solutions at 160° C. For the successive layers of CdS shell and ZnS shell, the cadmium and sulfur precursors were injected before the zinc and sulfur precursors. After the shell precursor addition was completed, the reaction flask was left at 160° C. for 10 min and then cooled at 90° C. for 30 min and further cooled to 40° C., at which point 2-3 ml of butanol (99.99%) were added. CdSe/CdS core/shell NCs were synthesized via the SILAR method (20). The shell synthesis and laser annealing used for CdSe/CdS/ZnS nanorods were performed using the protocol by Manna et al. (17).

Peptide Coating: A detailed procedure and schematic of peptide coating are found in ref. [15]. The following peptides were used to overcoat the NCs synthesized in this study:

```
                                              (SEQ.ID. NO. 2)
G-S-E-S-G-G-S-E-S-G-Cha-C-C-Cha-C-C-Cha-CC-Cha-
cmd;

(SEQ.ID. NO. 3)
Suc-G-S-S-S-G-G-S-S-S-G-Cha-C-C-Cha-C-C-Cha-CC-
Cha-cmd;

(SEQ.ID. NO. 5)
K-G-S-E-S-G-G-S-E-S-G-Cha-C-C-Cha-C-C-Cha-CC-Cha-
cmd;

(SEQ.ID. NO. 2)
Biotin-G-S-E-S-G-G-S-E-S-G-Cha-C-C-Cha-C-C-Cha-
CC-Cha-cmd;

(SEQ.ID. NO. 1)
PEG-Cha-C-C-Cha-C-C-Cha-CC-Cha-cmd.
```

Briefly, TOPO-coated core/shell NCs were precipitated with methanol and diluted with pyridine to 1 μM concentration. About 4.0 mg of peptides dissolved in 50 μl DMSO was mixed with 450 μL of the pyridine/NC solution. 12 μL of tetramethylammonium hydroxide (TMAOH) 25% (w/v) in methanol was added to the mixture in order to trigger the binding of the peptides to the NC surface. This mixture was then quickly vortexed and centrifuged, forming a NC precipitate. The NCs were redissolved in water and eluted through a G-25 Sephadex desalting column (Amersham, Piscataway, N.J.). The excess peptides in the mixture were removed through dialysis.

Fluorescence Correlation Spectroscopy: Fluorescence correlation spectroscopy (FCS) measurements were performed using a confocal excitation/detection scheme. Laser excitation of a femtoliter volume in a sample solution was provided by a Nd:YAG laser at 532 nm (Crystal Laser Inc.) with 1.5 μW excitation power (measured before entering a 1.2 NA water-immersion the objective). Fluorescence was detected in epi-configuration on an inverted microscope (Axiovert 100, Zeiss Inc.) equipped with a 50 μm pinhole. Using a non-polarizing beamsplitter, two avalanche photodiodes (AQR-13, Perkin Elmer Inc) and a hardware correlator (ALV, Germany), the cross-correlation was observed.

Photo-treatment: Graded shell CdSe/CdS/ZnS nanorods were photoannealed for 2-4 hours using 488 nm radiation from an argon ion laser at 25 mW. All other samples were irradiated with UV light for 40 minutes to several hours using a UV lamp with 366 nm radiation.

Quantum yield measurements: Quantum yields were acquired by exciting dye LD690 (63% QY) and the NC sample at the same OD at 500 nm, taking fluorescence spectra (corrected for detector efficiency), and comparing the integrated emission intensities. Errors were estimated to be between 5-10% of the evaluated QY.

The results of the above tests are summarized in Table 2. The results show the unexpected advantages provided by grading the shell composition and irradiating with UV light in accordance with the present invention. For example, the QY of graded shell CdSe/CdS/ZnS nanorods (sample #5) increased from 8% to 16% after laser annealing, showing similar results to previously reported laser annealing on CdSe/CdS/ZnS nanorods (17). Surprisingly, a similar increase of QY (from 1% to over 25%) was observed for graded shell CdSe/CdS/ZnS quantum dots (sample #2) when left several weeks to months in the dark in air, or in a much more accelerated fashion, after being exposed to UV illumination. Since the increase in QY is not necessarily light-driven, a possible explanation for this phenomenon could be a slow surface reconstruction (in the dark), which is accelerated by the illumination. Photo-annealing of defects in the shell may also be taking place with both laser and UV irradiation. On the other hand, UV irradiation of comparative NCs (Samples#1 and #4) while still in organic solvents did not significantly increase the QY, suggesting that binary shells may not be as easily photo-annealed. Since water solubilization of NCs is usually accompanied by a large QY loss, all samples were irradiated with UV/laser light prior to peptide coating.

For the CdSe/ZnS NCs sample (sample #1) QYs of 19% (in toluene, before peptide exchange) and 9% (in water, after peptide exchange) were measured, respectively. More typical QYs in water for other CdSe/ZnS samples were in the 1-2% range, with the largest QY losses for aged samples (>6 months) and thin shells (<3.5 monolayers). The CdSe/CdS (sample #4) and CdSe/CdS/ZnS layered (sample #3) samples also displayed low QY (<10%) after peptide exchange. Upon peptide coating, no spectral changes were observed for NCs having shell #1, while variations of emission peak position by 1 to 3 nm were detected for shells #3 and #4. For graded shell CdSe/CdS/ZnS NCs (sample #2) the measured QYs were 26% before peptide exchange and 24% after peptide exchange. For CdSe nanorods coated with a graded CdS/ZnS shell (sample #5), the measured QYs were 16% before peptide exchange and 8-9% after peptide exchange.

It was previously found that thin thiol coatings, such as the peptides used in the present invention, drastically decrease the QY of core/shell CdSe/ZnS and CdSe/CdS NCs (10, 15). In order to maintain better photoluminescence properties of water-soluble CdSe/ZnS, Kim et al. used thin coats made of oligomeric phosphine ligands to bind to the surface of these NCs, producing water-soluble NCs with relatively high quantum yield (14). The rationale behind their method was that the oligomeric phosphine ligands have multiple binding sites that passivate the surface of the NCs better than thiols. In these examples, we show that thiols do not necessarily cause a large decrease in quantum yield. Instead of optimizing ligands for better photoluminescence properties, the present invention modifies the shell composition and structure while using peptide ligands with the same hydrophobic binding domains.

As can be seen from Table 2, considerable permanent red shifts in both the absorption and emission peaks were observed for sample #2 (5-10 nm) and sample #5 (4-6 nm) Only small or no red shifts (0-3 nm) were observed for comparative samples #1, #3 and #4. The red shifts occurred either immediately following the completion of the peptide coating or eventually after long periods of time (weeks to months). These shifts to lower energy suggest that the exciton of the CdSe/CdS/ZnS NCs interacts with the MOs of the surface recognition domain in the peptide sequences. The broadening of the exciton peak in the absorption spectra, which is observed after peptide coating, in samples #2 and #5, also suggests a change in the interaction between excitonic states and the peptides. Talapin et al. have previously noticed a reversible shift in the emission peak of CdSe cores upon surface ligand exchange between TOPO and amines (21). They suggested that different passivating ligands redistribute electron density in the semiconductor. Here, however, noticeable red shifts were observed only for NCs with cadmium containing graded shells.

The graded CdS/ZnS ternary shells have a lower band gap and band offsets compared to ZnS binary shells. Alternatively, Cd could be considered as a dopant that introduces mid-gap states into the ZnS shell. In both cases, there is a higher probability that the electronic wavefunction would leak further out of the shell, permitting stronger interaction between the exciton and the MOs of the peptides. Peptides with different functional hydrophilic domains but identical adhesive hydrophobic domains resulted in the same red shifts. This implies that the hydrophobic C-terminal adhesive domain is responsible for the shift.

TABLE 2

| Sample | Emission Peak (nm) as synthesized (toluene) | Emission Peak (nm) w/peptides (water) | QY as synthesized (toluene) UV/ laser illum | QY w/peptides (water) no illum | QY w/peptides (water) UV illum. |
|---|---|---|---|---|---|
| #1 CdSe/ZnS | 613 | 613 | 19% | 1-9% | 9-15% |
| #2 CdSe/CdS/ZnS (graded) QDs | 620 | 625-630 | 26% | 15-24% | 20-35% |

TABLE 2-continued

| Sample | Emission Peak (nm) as synthesized (toluene) | Emission Peak (nm) w/peptides (water) | QY as synthesized (toluene) UV/ laser illum | QY w/peptides (water) no illum | QY w/peptides (water) UV illum. |
| --- | --- | --- | --- | --- | --- |
| #3 CdSe/CdS/ZnS (layered) | 622 | 624-625 | 14% | <1% | 1-2% |
| #4 CdSe/CdS | 620 | 622-623 | 35% | 2% | 2-3% |
| #5 CdSe/CdS/ZnS (graded) NRs | 648 | 652-654 | 16% | 8-9% | 10-13% |

In order to better characterize the fluorescence of the NCs synthesized in these examples in solution, we used fluorescence correlation spectroscopy (FCS) (22) (23). FCS was employed to study both the photophysical and colloidal properties of the NCs concurrently. Beyond providing an estimate of the diffusion constant, and hydrodynamic radius, correlation curves also provide information on the average number of NCs occupying the confocal volume (i.e. occupancy, or concentration). By normalizing the average count rate during the measurement to the occupancy, the brightness per particle (BPP) can be calculated. After peptide-coating, graded CdSe/CdS/ZnS NCs (sample #2) showed a BPP that is 40-50% higher than that of non-graded CdSe/ZnS NC's (sample #1). No signs of aggregation for either sample were detected.

The mechanism behind photo-induced QY increases with UV irradiation on NCs was studied on the ensemble level by absorption and emission spectroscopy and at low concentrations using FCS. Whereas ensemble absorption spectroscopy is sensitive to all NCs that absorb light, FCS is only sensitive to photoactive NCs (in the "on", or "bright" state). QYs of both samples #1 and #2 increased with UV irradiation (Table 2). These ensemble results were confirmed by FCS. BPP of peptide-coated non-graded CdSe/ZnS NC's (sample #1) increased through 40 min of UV irradiation with no appreciable change in concentration. In contrast, both the BPP and the concentration of particles with graded shells (sample #2) were increased upon UV irradiation. It is therefore likely that two mechanisms are responsible for the QY increase of sample #2: an increase in the intrinsic brightness of each NC and the activation of initially "dark" NC's to the "on" state. Evidence for "dark" NC's was recently reported using combined single-molecule fluorescence/AFM techniques (24). We also observed the photoactivation of core/shell NCs while imaging them by total internal reflection microscopy. Lastly, significantly larger saturation intensities were measured for the peptide-coated NCs in comparison to as-synthesized TBP/TOPO NC's.

The examples demonstrate that water-soluble peptide-coated NC's with modified graded CdS/ZnS shells have high QY that can be further enhanced by UV irradiation. The irradiation increases both the intrinsic brightness per particle and the number of bright particles in the sample. The resulting NC's are small, monodisperse, bioactive, very photostable, and have high QY. The enhanced properties make these probes suitable for single-molecule experiments in live cells (15). The examples also demonstrate water-solublization of nanorods (sample#5) using bioactivation peptides. These bioactivated nanorods can be used as orientational probes for studying rotational movements of macromolecules. It is expected that exciton-molecular orbital coupling might play an important role in determining the photophysical properties of these hybrid inorganic-organic composite materials, and that such coupling could be further improved by screening libraries of shell compositions and peptide sequences.

The graded shell in sample #2 may be applied to other cores in the same manner as set forth above. Examples of other cores include CdTeSe (heterogenous)[2] and alloyed cores of CdZnS and CdZnSe[25, 26].

Although the foregoing invention has been described in some detail for purposes of clarity of understanding, those skilled in the art will appreciate that various adaptations and modifications of the just described preferred embodiments can be configured without departing from the scope and spirit of the invention. The described embodiments should be taken as illustrative and not restrictive, and the invention should not be limited to the details given herein but should be defined by the following claims and their full scope of equivalents.

BIBLIOGRAPHY

1. Michalet, X., Pinaud, F., Lacoste, T. D., Dahan, M., Bruchez, M. P., Alivisatos, A. P. & Weiss, S. (2001) *Single Molecules* 2, 261-276.
2. Alivisatos, P. (2004) *Nature Biotechnology* 22, 47-52.
3. Peng, X., Schlamp, M. C., Kadavanich, A. V. & Alivisatos, A. P. (1997) *Journal of the American Chemical Society* 119, 7019-7029.
4. Hines, M. A. & Guyot-Sionnest, P. (1996) *Journal of Physical Chemistry* 100, 468-471.
5. Dabbousi, R. O., Rodriguez-Viejo, J., Mikulec, F. V., Heine, J. R., Mattoussi, H., Ober, R., Jensen, K. F. & Bawendi, M. G. (1997) *Journal of Physical Chemistry B* 101, 9463-9475.
6. Tsay, J. M., Pflughoefft, M., Bentolila, L. A. & Weiss, S. (2004) *Journal of the American Chemical Society* 126, 1926-1927.
7. Bruchez, M., Moronne, M., Gin, P., Weiss, S. & Alivisatos, A. P. (1998) *Science* 281, 2013-2016.
8. Gerion, D., Pinaud, F., Williams, S. C., Parak, W. J., Zanchet, D., Weiss, S. & Alivisatos, A. P. (2001) *Journal of Physical Chemistry B* 105, 8861-8871.
9. Chan, W. C. W. & Nie, S. M. (1998) *Science* 281, 2016-2018.
10. Guo, W., Li, J. J., Wang, Y. A. & Peng, X. (2003) *J Am Chem Soc* 125, 3901-9.
11. Larson, D. R., Zipfel, W. R., Williams, R. M., Clark, S. W., Bruchez, M. P., Wise, F. W. & Webb, W. W. (2003) *Science* 300, 1434-6.
12. Dubertret, B., Skourides, P., Norris, D. J., Noireaux, V., Brivanlou, A. H. & Libchaber, A. (2002) *Science* 298, 1759-62.
13. Mattoussi, H., Mauro, J. M., Goldman, E. R., Green, T. M., Anderson, G. P., Sundar, V. C. & Bawendi, M. G. (2001) *Physica Status Solidi B-Basic Research* 224, 277-283.
14. Kim, S. & Bawendi, M. G. (2003) *J Am Chem Soc* 125, 14652-3.

15. Pinaud, F. K., D.; Moore, H.; Weiss, S. (2004) *J. Am. Chem. Soc.* 126, 6115-6123.
16. Michalet, X. & Doose, S. *unpublished results*.
17. Manna, L., Scher, E. C., Li, L. S. & Alivisatos, A. P. (2002) *Journal of the American Chemical Society* 124, 7136-7145.
18. Murray, C. B., Norris, D. J. & Bawendi, M. G. (1993) *Journal of the American Chemical Society* 115, 8706-8715.
19. Peng, Z. A. & Peng, X. G. (2002) *Journal of the American Chemical Society* 124, 3343-3353.
20. Li, J. J., Wang, Y. A., Guo, W. Z., Keay, J. C., Mishima, T. D., Johnson, M. B. & Peng, X. G. (2003) *Journal of the American Chemical Society* 125, 12567-12575.
21. Talapin, D. V., Rogach, A. L., Kornowski, A., Haase, M. & Weller, H. (2001) *Nano Letters* 1, 207-211.
22. Magde, D., Elson, E. L. & Webb, W. W. (1974) *Biopolymers* 13, 29-61.
23. Rigler, R., Mets, U., Widengren, J. & Kask, P. (1993) *European Biophysics Journal* 22, 169-175.
24. Ebenstein, Y., Mokari, T. & Banin, U. (2002) *Applied Physics Letters* 80, 4033-4035.

What is claimed is:

1. A peptide-coated nanoparticle comprising:
    a spherical nanocrystal core surrounded by a graded shell wherein said graded shell comprises at least two different semiconductor molecules; and
    at least one peptide attached to a surface of said graded shell.

2. A peptide-coated nanoparticle according to claim 1 wherein said spherical nanocrystal core is a crystal having a diameter of from 1 to 10 nanometers.

3. A peptide-coated nanoparticle according to claim 1 wherein said graded shell comprises two different semiconductor molecules selected from the group consisting of ZnS, CdS, ZnSe and CdSe.

4. A peptide-coated nanoparticle according to claim 1 wherein said spherical nanocrystal core comprises one or more semiconductor molecules selected from group of molecules consisting of elements from columns II-IV, III-V or IV of the periodic table.

5. A peptide-coated nanoparticle according to claim 1 wherein said spherical nanocrystal core comprises CdSe.

6. A peptide-coated nanoparticle according to claim 1 wherein said graded shell comprises ZnS and CdS molecules.

7. A peptide-coated nanoparticle according to claim 1 wherein said graded shell comprises from 1 to 10 monolayers.

8. A peptide-coated nanoparticle according to claim 1 wherein a diameter of said spherical nanocrystal core is from 4 to 5 nanometers and said graded shell comprises from 3 to 6 monolayers.

9. A peptide-coated nanoparticle according to claim 1 wherein said peptide attached to the surface of said graded shell comprises:
    a surface recognition part that is bound to the surface of said graded shell and one or more functional parts, said surface recognition part including an amino-end and a carboxy-end and comprising one or more hydrophobic spacers and one or more binding clusters and wherein said functional part(s) is attached to said surface recognition part at said amino-end and/or said carboxy-end.

10. A peptide-coated nanoparticle according to claim 9 wherein said binding cluster comprises an amino acid selected from the group consisting of cysteine, methionine, histidine and derivatives thereof.

11. A peptide-coated nanoparticle according to claim 10 where said binding cluster consists essentially of two cysteines.

12. A peptide-coated nanoparticle according to claim 9 wherein said hydrophobic spacer is a hydrophobic amino acid selected from the group consisting of hydrophobic alanine, hydrophobic glycine, hydrophobic isoleucine, hydrophobic leucine, hydrophobic methionine, hydrophobic arginine, hydrophobic valine, hydrophobic tryptophan and derivatives thereof.

13. A peptide-coated nanoparticle according to claim 12 wherein said hydrophobic amino acid is hydrophobic alanine.

14. A peptide-coated nanoparticle according to claim 13 wherein said hydrophobic alanine is cyclohexyl-substituted alanine.

15. A peptide-coated nanoparticle according to claim 9 wherein said surface recognition part comprises at least three binding clusters which are alternately located between at least four hydrophobic spacers.

16. A peptide-coated nanoparticle according to claim 15 wherein said binding clusters each consists essentially of two cysteines and said hydrophobic spacers each consists essentially of cyclohexyl-substituted alanine.

17. A peptide-coated nanoparticle according to claim 9 wherein said functional part(s) comprises one or more functional agent(s) selected from the group consisting of solubility agents, conjugation agents, targeting agents, therapeutic agents, imaging agents, detection agents, recognition agents and diagnostic agents.

18. A peptide-coated nanoparticle according to claim 1 wherein said spherical nanocrystal core surrounded by said graded shell is annealed with ultra violet radiation prior to and/or after attachment of said peptide to the surface of said graded shell.

* * * * *

UNITED STATES PATENT AND TRADEMARK OFFICE
CERTIFICATE OF CORRECTION

PATENT NO. : 8,383,423 B2  
APPLICATION NO. : 13/074209  
DATED : February 26, 2013  
INVENTOR(S) : Weiss et al.

Page 1 of 1

It is certified that error appears in the above-identified patent and that said Letters Patent is hereby corrected as shown below:

In the specification:

Column 1, lines 4 – 13 should read,

--This application is a Continuation Application of U.S. patent application Ser. No. 11/630,584, filed Dec. 22, 2006, which is a National Stage of International Application Number PCT/US2005/022102, filed Jun. 20, 2005, which claims the benefit of U.S. Provisional Application Number 60/581,828, filed Jun. 22, 2004. This invention was made with Government support under Grant Nos. EB000312 and RR014891, awarded by the National Institutes of Health and Grant No. DE-AC02-05CH11231, awarded by the Department of Energy. The Government has certain rights in this invention.--.

Signed and Sealed this  
Tenth Day of February, 2015

Michelle K. Lee  
*Deputy Director of the United States Patent and Trademark Office*